(12) United States Patent
Trieu

(10) Patent No.: US 8,974,502 B2
(45) Date of Patent: Mar. 10, 2015

(54) METHODS, SYSTEMS, AND DEVICES FOR TREATING INTERVERTEBRAL DISCS INCLUDING INTRADISCAL FLUID EVACUATION

(75) Inventor: Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1670 days.

(21) Appl. No.: 12/261,601

(22) Filed: Oct. 30, 2008

(65) Prior Publication Data

US 2010/0114069 A1   May 6, 2010

(51) Int. Cl.
*A61B 17/56* (2006.01)
*A61F 2/44* (2006.01)
*A61B 17/70* (2006.01)
*A61B 17/88* (2006.01)
*A61F 2/30* (2006.01)

(52) U.S. Cl.
CPC .............. *A61F 2/441* (2013.01); *A61B 17/7097* (2013.01); *A61B 17/8811* (2013.01); *A61B 17/8825* (2013.01); *A61F 2002/30062* (2013.01); *A61F 2002/30583* (2013.01); *A61F 2002/444* (2013.01); *A61F 2210/0004* (2013.01); *A61F 2210/0085* (2013.01)
USPC .......................................... 606/279; 604/500

(58) Field of Classification Search
USPC ............. 606/92, 279; 128/898; 604/500, 506; 623/17.16
See application file for complete search history.

(56) References Cited

U.S. PATENT DOCUMENTS

| | | | |
|---|---|---|---|
| 5,192,282 A * | 3/1993 | Draenert | 606/65 |
| 5,643,304 A | 7/1997 | Schechter et al. | |
| 6,370,420 B1 * | 4/2002 | Kraft | 600/431 |
| 8,337,557 B2 * | 12/2012 | Collins et al. | 623/17.12 |
| 2002/0052620 A1 * | 5/2002 | Barbut | 606/190 |
| 2004/0054414 A1 * | 3/2004 | Trieu et al. | 623/17.16 |
| 2004/0186471 A1 * | 9/2004 | Trieu | 606/61 |
| 2004/0243137 A1 * | 12/2004 | Gorek | 606/92 |
| 2005/0119754 A1 | 6/2005 | Trieu et al. | |
| 2005/0197707 A1 | 9/2005 | Trieu et al. | |
| 2006/0224160 A1 | 10/2006 | Trieu et al. | |
| 2006/0276802 A1 * | 12/2006 | Vresilovic et al. | 606/102 |
| 2007/0100349 A1 | 5/2007 | O'Neil et al. | |
| 2007/0150060 A1 | 6/2007 | Trieu | |
| 2007/0150061 A1 | 6/2007 | Trieu | |
| 2007/0255285 A1 | 11/2007 | Trieu | |
| 2007/0255286 A1 | 11/2007 | Trieu | |
| 2007/0255406 A1 | 11/2007 | Trieu | |
| 2007/0299426 A1 | 12/2007 | Trieu et al. | |
| 2008/0004570 A1 | 1/2008 | Simonton et al. | |
| 2008/0004703 A1 | 1/2008 | Trieu et al. | |
| 2008/0071281 A1 | 3/2008 | Wilson et al. | |
| 2008/0275395 A1 * | 11/2008 | Asbury et al. | 604/113 |

\* cited by examiner

*Primary Examiner* — Nicholas Woodall
*Assistant Examiner* — Larry E Waggle, Jr.
(74) *Attorney, Agent, or Firm* — Sorell Lenna & Schmidt LLP

(57) ABSTRACT

Methods, systems, and devices for of treating intervertebral discs are disclosed. In one embodiment, a minimally invasive method of treating an intervertebral disc is provided. A contrast or imaging media is introduced into a nucleus of the intervertebral disc without removing any of the nucleus. The intervertebral disc is imaged with the contrast media within the nucleus. Then the contrast media is evacuated from the nucleus to reduce intradiscal pressure. Finally, a disc augmentation biomaterial is introduced into the nucleus. The disc augmentation biomaterial is introduced in such a manner that the disc augmentation biomaterial is maintained within the nucleus without having to repair an opening in the annulus surrounding the nucleus.

18 Claims, 11 Drawing Sheets

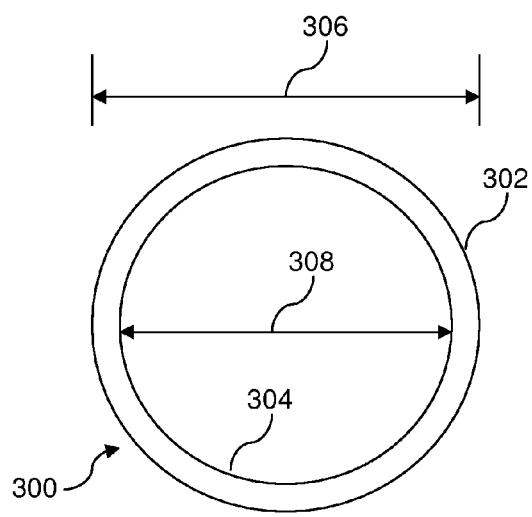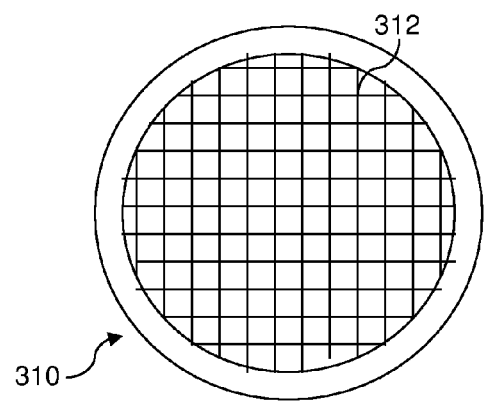
FIG. 9          FIG. 10
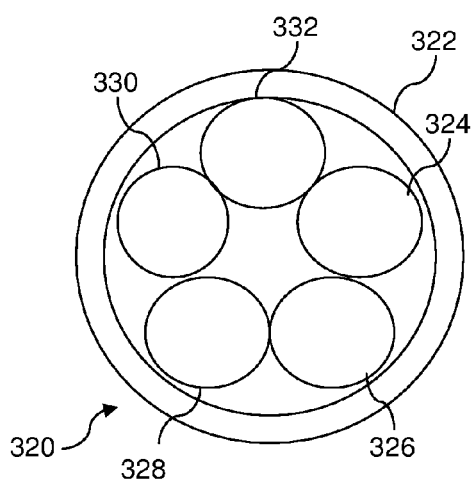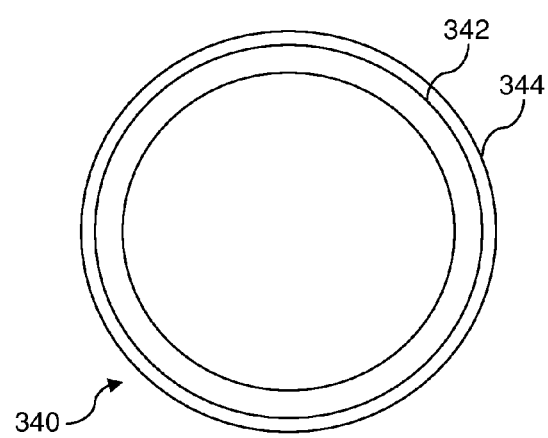
FIG. 11         FIG. 12

METHODS, SYSTEMS, AND DEVICES FOR TREATING INTERVERTEBRAL DISCS INCLUDING INTRADISCAL FLUID EVACUATION

BACKGROUND

Within the spine, the intervertebral disc functions to stabilize and distribute forces between vertebral bodies. The intervertebral disc comprises a nucleus pulposus which is surrounded and confined by the annulus fibrosis. Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration are frequently treated by replacing or augmenting the existing disc material. Current methods and instrumentation used for treating the disc require a relatively large hole to be cut in the disc annulus to allow introduction of the implant. After the implantation, the large hole in the annulus must be plugged, sewn closed, blocked or otherwise repaired to avoid allowing the implant to be expelled from the disc. Besides weakening the annular tissue, creation of the large opening and the subsequent repair adds surgical time and cost. Further, many disc augmentation procedures require a discography or other imaging of the patient's intervertebral disc prior to the augmentation procedure. In that regard, the discography typically involves introducing a contrast media into the intervertebral disc space. It takes several hours or even days for the contrast media to diffuse out of the intervertebral disc and for the intradiscal pressure to go back to the level present before the discography. Accordingly, a need exists for improved methods, systems, and apparatus for treating an intervertebral disc using minimally invasive surgical techniques.

SUMMARY

In some embodiments, minimally invasive methods of treating an intervertebral disc are provided.

In one embodiment, a method of treating an intervertebral disc of a patient is provided. The method includes introducing a contrast media through an annulus and into a nucleus of the intervertebral disc via a hypodermic needle. The contrast media is introduced without any of the annulus or nucleus being removed beforehand. The method also includes imaging the intervertebral disc with the contrast media within the nucleus and evacuating the contrast media and other flowable material from the nucleus via vacuum extraction. The vacuum extraction is applied to the nucleus through a hypodermic needle. The hypodermic needle includes a distal portion for positioning within the nucleus and an opposing proximal portion for positioning outside the intervertebral disc. The proximal portion of the needle is in communication with a reservoir for receiving the evacuated contrast media and flowable material. Finally, the method includes introducing a disc augmentation biomaterial into the nucleus through the annulus and into the nucleus of the intervertebral disc via a hypodermic needle such that the disc augmentation biomaterial is maintained within the nucleus without having to repair an opening in the annulus.

In some instances, the same needle is used for both introducing the contrast media and evacuating the contrast media. The needle used for both introducing the contrast media and evacuating the contrast media is retracted from the intervertebral disc before the imaging step in some instances. At least a portion of the needle used for both introducing the contrast media and evacuating the contrast media is positioned within the patient during the imaging step in some instances. In such instances, at least a portion of the needle used for both introducing the contrast media and evacuating the contrast media is reintroduced into the nucleus after the imaging step. Evacuating the contrast media and other flowable material from the nucleus comprises moving the needle around within the nucleus in some instances. Also, in some instances, the vacuum extraction is applied intermittently to prevent clogging of the needle. The vacuum extraction is applied via a vacuum source in communication with the reservoir in some instances. In some embodiments, introducing the disc augmentation biomaterial into the nucleus comprises injecting a collagen-based material into the nucleus. In some embodiments, introducing the disc augmentation biomaterial into the nucleus comprises injecting the disc augmentation material into an inflatable balloon positioned within the nucleus.

In another embodiment, a method of treating an intervertebral disc of a patient is provided. The method comprises introducing a contrast media into a nucleus of the intervertebral disc. The contrast media is introduced without removing any of the nucleus. The method also comprises imaging the intervertebral disc with the contrast media within the nucleus and aspirating at least the contrast media from the nucleus to reduce an intradiscal pressure within the nucleus. The method also comprises introducing a disc augmentation biomaterial into the nucleus. The disc augmentation biomaterial is introduced in a manner such that the disc augmentation biomaterial is maintained within the nucleus without having to repair an opening in an annulus surrounding the nucleus.

In some instances, introducing the disc augmentation material into the nucleus comprises introducing the disc augmentation material until the intradiscal pressure reaches a predetermined range. In some instances, the contrast media is aspirated through a cannula via vacuum suction to a reservoir. In some instances, the cannula comprises a filter at a distal end to limit the aspiration to flowable materials and prevent aspiration of solid tissue larger than a predetermined size. In some embodiments, the filter prevents aspiration of solid tissue with a diameter larger than about 0.5 mm. In some instances aspirating the flowable materials from the nucleus comprises moving the cannula around within the nucleus. Further, in some instances the vacuum suction is applied intermittently to prevent clogging of the filter. In some embodiments, the cannula comprises a plurality of openings to enhance aspiration and prevent clogging of the cannula.

In another embodiment, a surgical method is provided. The method comprises introducing a radiopaque contrast media into a nucleus of an intervertebral disc via a transannular approach. The radiopaque contrast media is injected through a hypodermic needle without prior removal of any of the nucleus or an annulus surrounding the nucleus. Introducing the radiopaque contrast media into the nucleus increases an intradiscal pressure within the nucleus. The method also comprises imaging the intervertebral disc with the contrast media within the nucleus and aspirating the contrast media and other flowable material from the nucleus via vacuum extraction to reduce the intradiscal pressure within the nucleus. The vacuum extraction is applied to the nucleus through a hypodermic needle having a maximum outer diameter less than about 0.9 mm and an inner diameter of less than about 0.6 mm to prevent removal of solid tissue with a diameter larger than about 0.6 mm. The hypodermic needle has a distal portion for positioning within the nucleus and an opposing proximal portion for positioning outside the intervertebral disc. The proximal portion of the needle is in communication with a vacuum source for selectively applying the vacuum extraction and in communication with a reservoir for receiving the evacuated contrast media and flowable material. The distal portion of the hypodermic needle is moved around the nucleus during aspiration and the vacuum extraction is applied intermittently to prevent clogging of the hypodermic needle. The method also comprises introducing a disc augmentation biomaterial into the nucleus through the annulus and into the nucleus of the intervertebral disc via a hypodermic needle such that the disc augmentation biomaterial is maintained within the nucleus without having to repair an opening in the annulus. The disc augmentation biomaterial is introduced until the intradiscal pressure reaches a predetermined range. In some instances, the method further comprises monitoring the flow of the radiopaque contrast media through the nucleus with an imaging device during introduction of the radiopaque contrast media.

Additional embodiments are included and will be apparent from the attached drawings and the detailed description provided below.

BRIEF DESCRIPTION OF THE DRAWINGS

FIG. 9 is a diagrammatic end view of a needle according to one aspect of the present disclosure.

FIG. 10 is a diagrammatic end view of a needle similar to that of FIG. 9, but showing an alternative aspect of the present disclosure.

FIG. 11 is a diagrammatic end view of a needle similar to that of FIGS. 9 and 10, but showing an alternative aspect of the present disclosure.

FIG. 12 is a diagrammatic end view of a needle similar to that of FIGS. 9-11, but showing an alternative aspect of the present disclosure.

DETAILED DESCRIPTION

Figure 1:
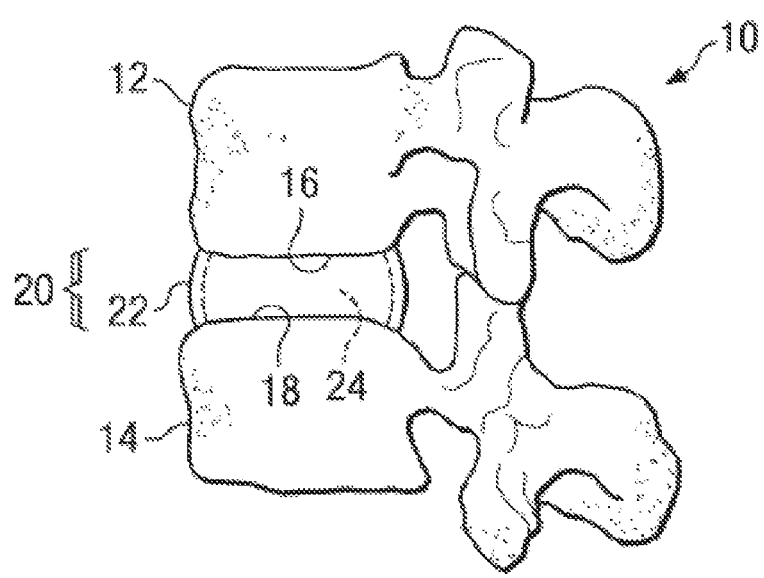
FIG. 1 is a diagrammatic sagittal view of a portion of a vertebral column.

The present disclosure relates generally to methods, systems, and apparatus for treating an intervertebral disc, and more particularly, to methods, systems, and apparatus for minimally invasive procedures. For the purposes of promoting an understanding of the principles of the present disclosure, reference will now be made to the embodiments, or examples, illustrated in the drawings and specific language will be used to describe the same. It will nevertheless be understood that no limitation of the scope of the present disclosure is thereby intended. Any alterations and further modifications in the described embodiments, and any further applications of the principles of the invention as described herein are fully contemplated as would normally occur to one skilled in the art to which the disclosure relates.

Referring first to FIG. 1, a vertebral joint section or a motion segment 10 of a vertebral column is shown. The joint section 10 includes adjacent vertebral bodies 12, 14. The vertebral bodies 12, 14 include endplates 16, 18, respectively. An intervertebral disc space 20 is located between the endplates 16, 18. The intervertebral disc space 20 includes an annulus 22 extending around its perimeter. In a healthy joint, the intervertebral disc space 20 contains a nucleus pulposus 24.

Figure 2:
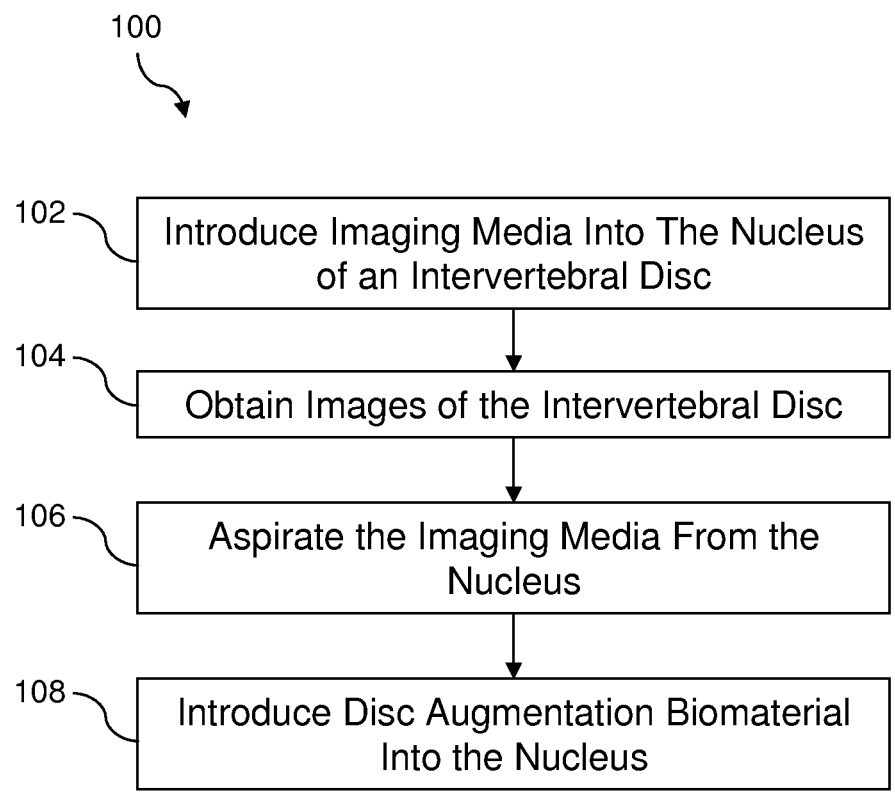
FIG. 2 is a flowchart illustrating a method of treating an intervertebral disc according to one aspect of the present disclosure.
Figure 3:
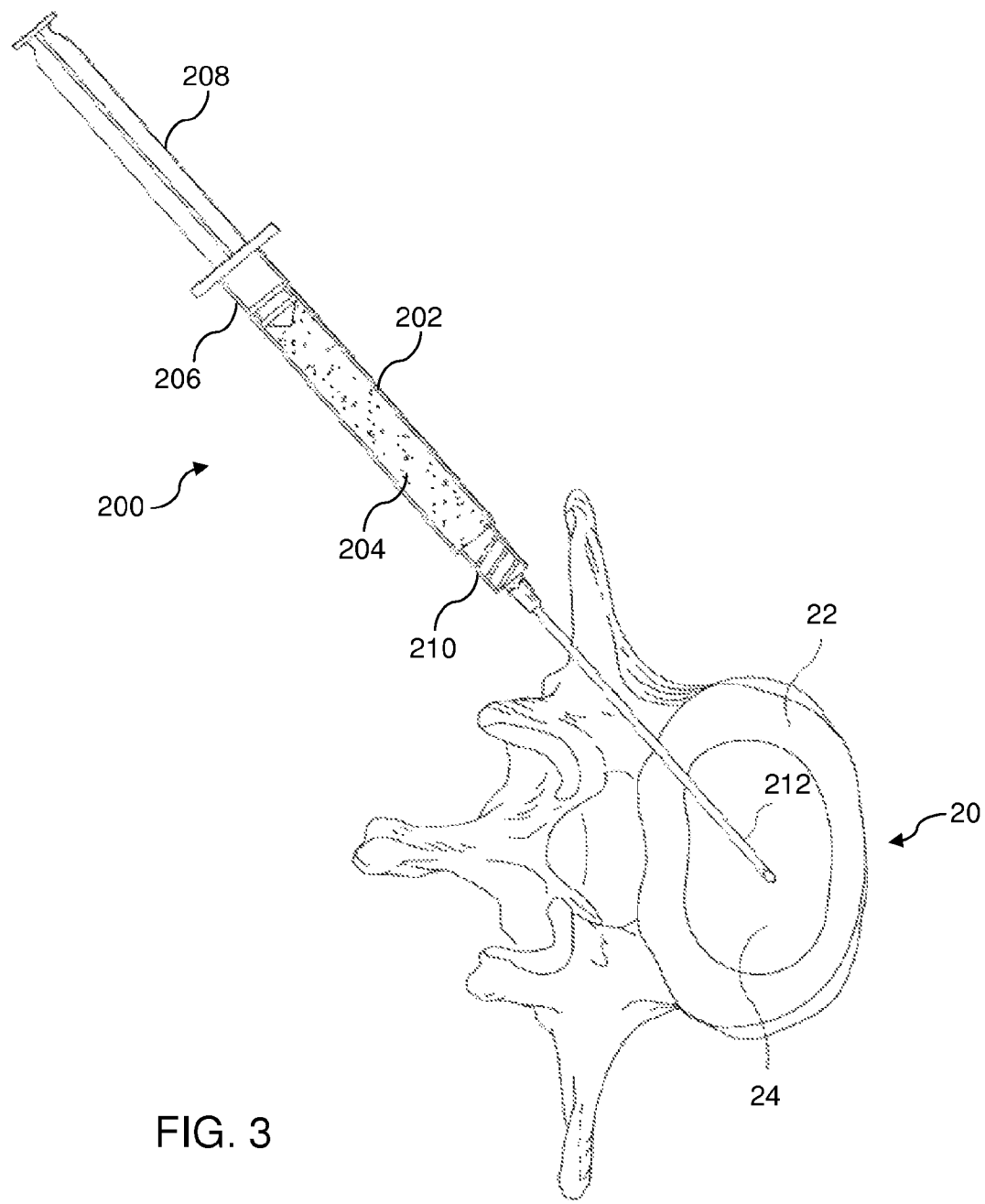
FIG. 3 is a diagrammatic top view of an intervertebral disc illustrating a step of the method of FIG. 2.
Figure 4:
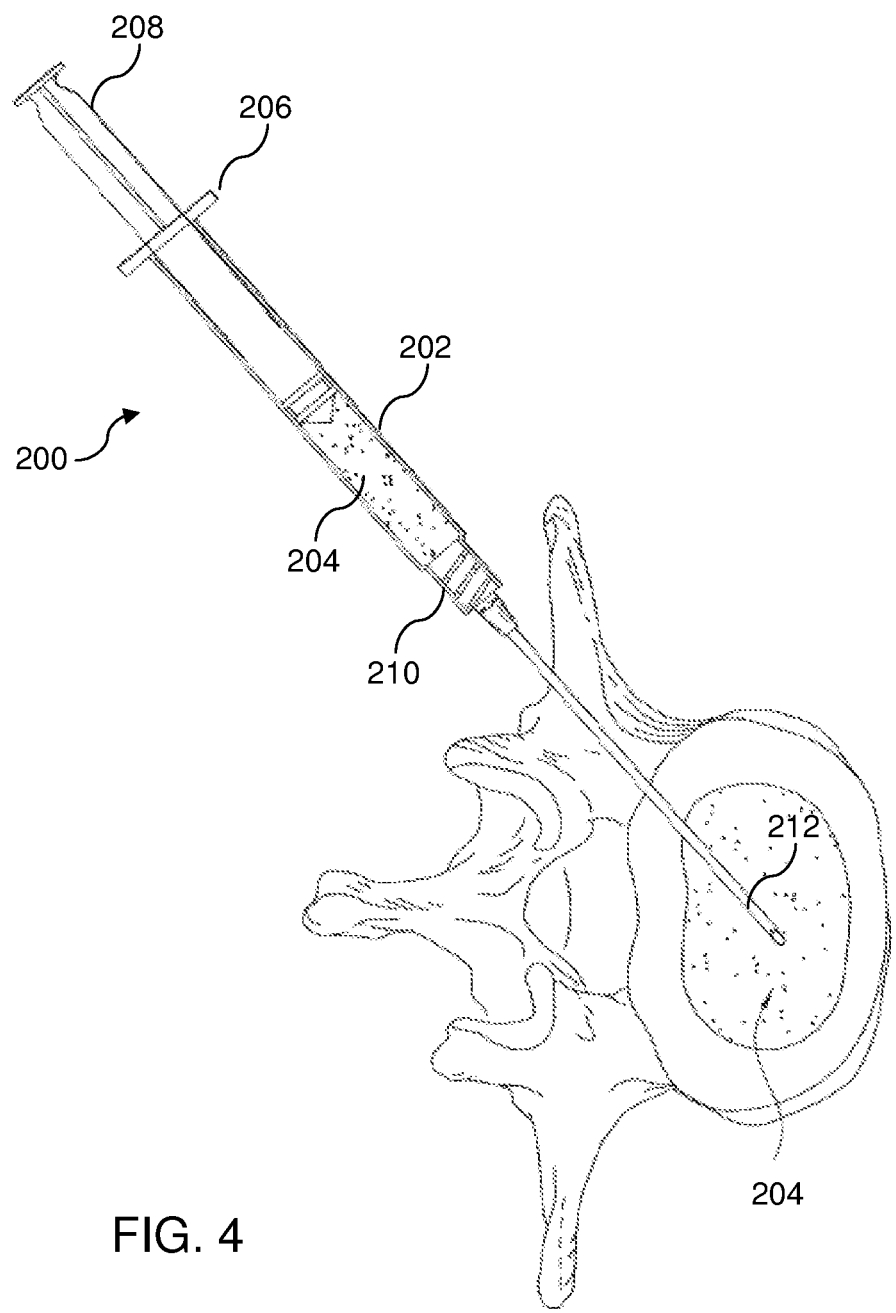
FIG. 4 is a diagrammatic top view of an intervertebral disc similar to that of FIG. 3, but illustrating a subsequent step of the method of FIG. 2.
Figure 5:
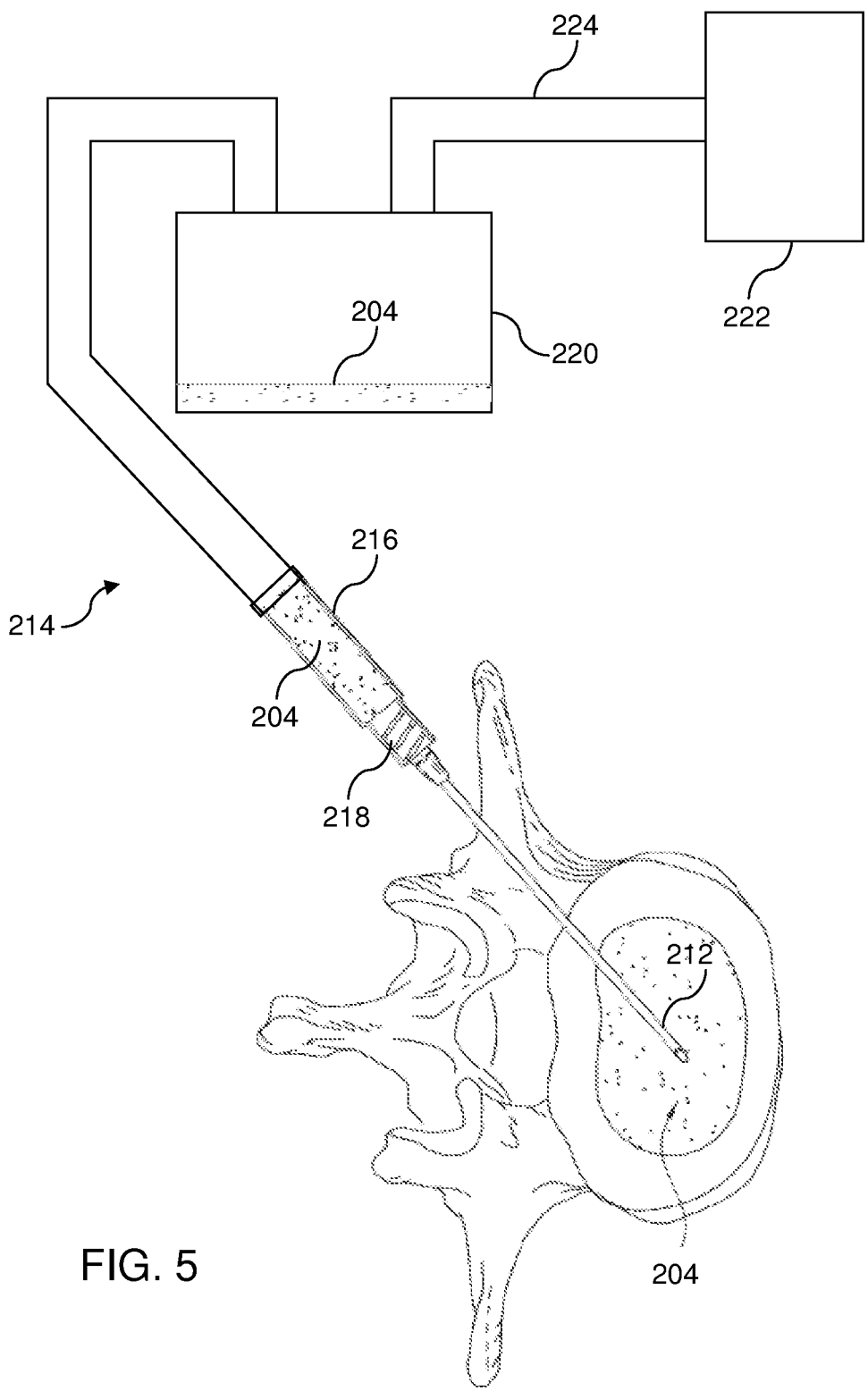
FIG. 5 is a diagrammatic top view of an intervertebral disc similar to that of FIGS. 3 and 4, but illustrating a subsequent step of the method of FIG. 2.
Figure 6:
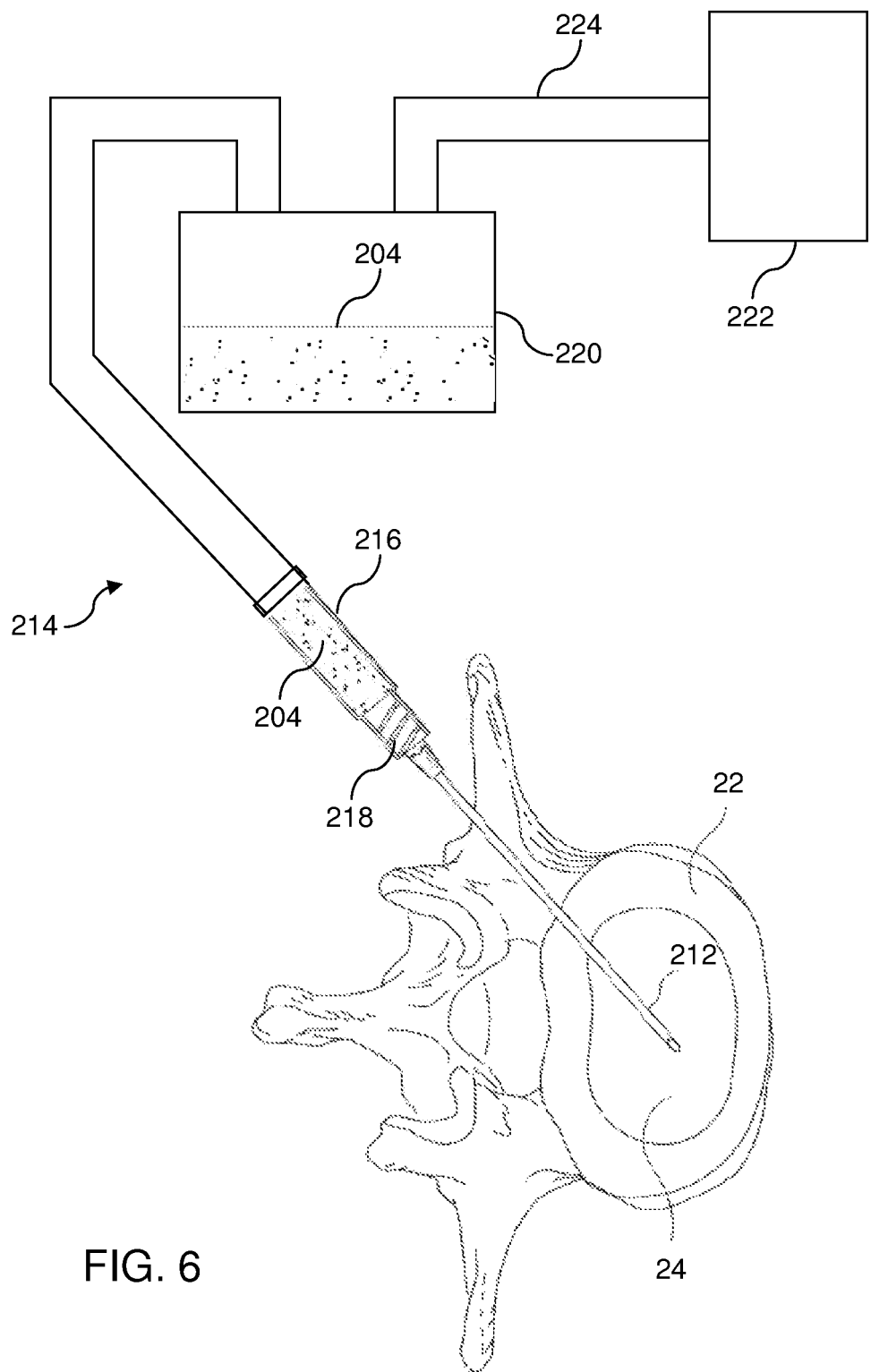
FIG. 6 is a diagrammatic top view of an intervertebral disc similar to that of FIGS. 3-5, but illustrating a subsequent step of the method of FIG. 2.
Figure 7:
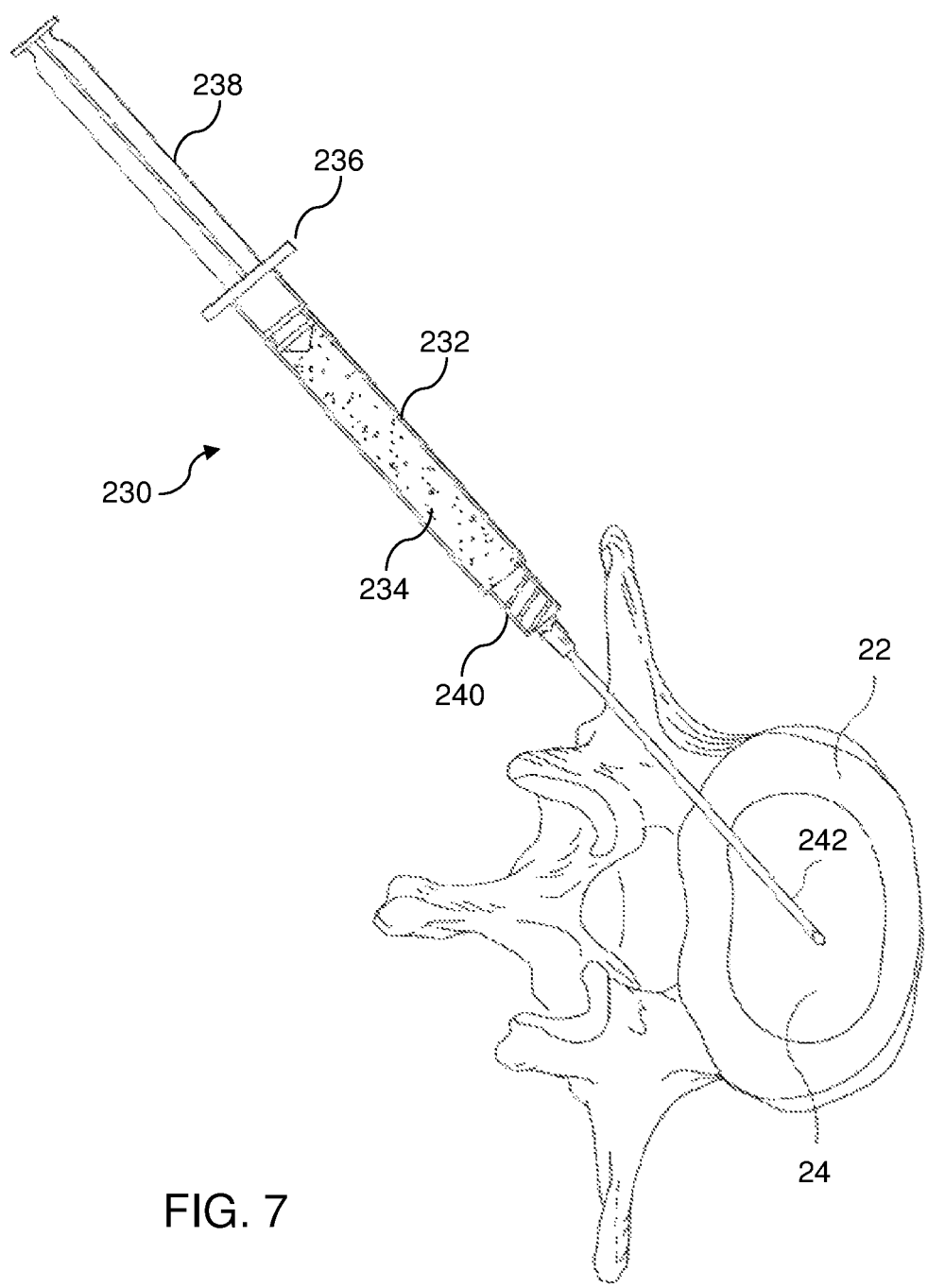
FIG. 7 is a diagrammatic top view of an intervertebral disc similar to that of FIGS. 3-6, but illustrating a subsequent step of the method of FIG. 2.
Figure 8:
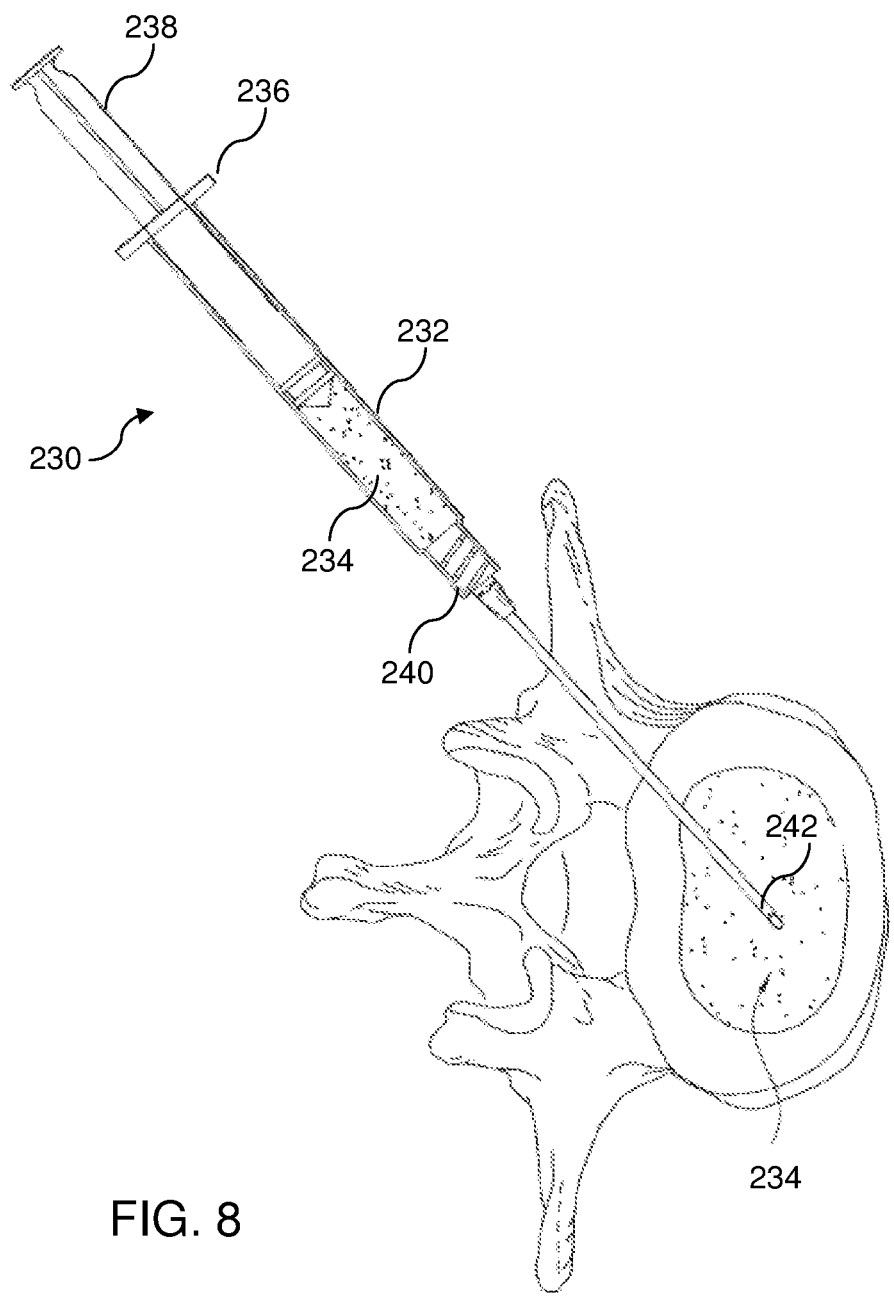
FIG. 8 is a diagrammatic top view of an intervertebral disc similar to that of FIGS. 3-7, but illustrating a subsequent step of the method of FIG. 2.

Referring now to FIGS. 2-8, a method 100 for treating an intervertebral disc according to one aspect of the present disclosure is illustrated. In particular, FIG. 2 is a flowchart illustrating generally the steps of the method 100. FIGS. 3-8 are a sequence of views illustrating steps of the method 100. In that regard, FIG. 3 is a top view of an intervertebral disc illustrating a step of the method 100; FIG. 4 is a top view of an intervertebral disc similar to that of FIG. 3, but illustrating a subsequent step of the method 100; FIG. 5 is a top view of an intervertebral disc similar to that of FIGS. 3 and 4, but illustrating a subsequent step of the method 100; FIG. 6 is a top view of an intervertebral disc similar to that of FIGS. 3-5, but illustrating a subsequent step of the method 100; FIG. 7 is a top view of an intervertebral disc similar to that of FIGS. 3-6, but illustrating a subsequent step of the method 100; and FIG. 8 is a top view of an intervertebral disc similar to that of FIGS. 3-7, but illustrating a subsequent step of the method 100.

Referring more specifically to FIG. 2, the method 100 begins at step 102 wherein an imaging media is introduced into the nucleus of an intervertebral disc. In that regard, the imaging media is a material suitable for use in obtaining images of the intervertebral disc and, in particular, the nucleus of the intervertebral disc. In some instances, the imaging media is a contrast media utilized in discography procedures. In some instances, the imaging media is a radiopaque material, such as barium sulfate, or includes a radiopaque material, such as HYPAQUE®, Omnipaque™, and/or tantalum powder suspension. In some instances, the imaging media is a saline solution that comprises a radiocontrast material.

Referring to FIG. 3, in some instances an injector 200 is utilized at step 102. In the illustrated embodiment, the injector 200 comprises a main body 202 that houses an imaging media 204. A proximal portion 206 of the main body 202 receives a plunger 208 that is moveable along the longitudinal axis of the main body to urge the imaging media 204 out of a distal portion 210 of the main body 202. In the illustrated embodiment, the distal portion 210 of the main body 202 is engaged with a hypodermic needle 212. In particular, the distal portion 210 of the main body 202 is threadingly engaged with a hypodermic needle 212. Accordingly, the imaging media 204 that is urged out of the distal portion 210 of the main body 202 passes into the needle 212 upon distal advancement of the plunger 208 into the main body.

The injector 200 is utilized to introduce the imaging media into the nucleus 24 of the intervertebral disc 20 in some instances. In that regard, the hypodermic needle 212 is advanced through the annulus 22 and into the nucleus 24 as shown in FIG. 3. Once the distal end of the needle 212 is positioned within the nucleus 24, the plunger 208 is depressed to inject the imaging media 204 into the nucleus. In some instances, the distal end of the needle 212 is moved around within the nucleus 24 during injection of the imaging media 204 to encourage distribution of the imaging media throughout the nucleus. In some instances the imaging media is introduced without removing any of the nucleus 24 beforehand. That is, a partial or total nucleotomy is not performed prior to injection of the imaging media 204 in some instances. This allows preservation of a maximum amount of the patient's natural tissue. In some instances, prior to introduction of the imaging media 204 an inflatable device is introduced into the nucleus 24 and expanded. In this manner the inflatable device is utilized to create a space within the nucleus 24 and/or reshape the natural nucleus material without removing any of the nucleus.

Examples of using an inflatable device for creating space within a nucleus are disclosed in U.S. patent application Ser. No. 10/314,396 titled "Method and Apparatus for Intervertebral Disc Expansion" and filed Dec. 7, 2002; U.S. patent application Ser. No. 11/412,272 titled "Devices, Apparatus, and Methods for Bilateral Approach to Disc Augmentation" and filed Apr. 27, 2006; U.S. patent application Ser. No. 11/412,558 titled "Devices, Apparatus, and Methods for Improved Disc Augmentation" and filed Apr. 27, 2006; U.S. patent application Ser. No. 11/621,173 titled "Devices, Apparatus, and Methods for Disc Augmentation" and filed Jan. 9, 2007; and U.S. patent application Ser. No. 11/924,026 titled "Method and Apparatus for Intervertebral Disc Expansion" and filed Oct. 25, 2007, each of which is hereby incorporated by reference in its entirety.

Generally, the expandable device or balloon may be formed of elastic or non-elastic materials. Further, the expandable device can be of various shapes including conical, spherical, square, long conical, long spherical, long square, tapered, stepped, dog bone, offset, or combinations thereof. Expandable devices can be made of various polymeric materials such as polyethylene terephthalates, polyolefins, polyurethanes, nylon, polyvinyl chloride, silicone, polyetheretherketone, polylactide, polyglycolide, poly(lactide-co-glycoli-de), poly(dioxanone), poly(.epsilon.-caprolactone), poly(hydroxylbutyrate), poly(hydroxylvalerate), tyrosine-based polycarbonate, polypropylene fumarate, and/or combinations thereof. Additionally, the expandable device may be molded or woven in some instances.

In other embodiments, a mechanical instrument, such as a probe or a tamp, is utilized to create a space within the nucleus 24 and/or reshape the natural nucleus material without removing any of the nucleus. In some instances, a mechanically actuated, deformable or expandable instrument that deforms via hinges, springs, shape memory material, etc. is used to create the space. The passage of the expandable device and/or mechanical instruments to the nucleus 24 are aided by a more rigid guide needle or cannula in some instances. This guide is removed after the expandable device and/or mechanical instruments are located within the nucleus 24. While in many instances it is preferable to preserve the natural nucleus, or what remains of it after natural disease or degeneration, as described above, in other instances a partial or complete nucleotomy is performed prior to injection of the imaging media 204.

In some embodiments, the nucleus 24 is accessed by inserting a cannula or guide sheath (not shown) into the patient and locating the cannula at or near the annulus 22. In some instances, the needle 212 is advanced through the cannula or guide sheath before piercing the annulus 22 to reach the nucleus 24. In other instances, an accessing instrument, such as a trocar needle or a K-wire is inserted through the cannula and used to penetrate the annulus, creating an opening in the annulus 22 through which the needle 212 will be introduced into the nucleus 24. It is understood that any cannulated instrument including a guide needle or a trocar sleeve may be used to guide the accessing instrument.

In the illustrated embodiment, the nucleus 24 is accessed by the needle 212 using an oblique posterior unilateral approach. In alternative embodiments, the nucleus 24 is accessed with a lateral approach, a posterior approach, an anterior approach, an oblique approach, a trans-pedicular approach, and/or any other suitable nucleus accessing approach. For example, in one alternative embodiment, the nucleus 24 is accessed through one the of vertebral bodies 12, 14 and through its respective endplate 16, 18. Further, although a unilateral approach is described and illustrated, bilateral and multi-lateral approaches are utilized in other instances. In that regard, multiple injectors 200 are utilized to inject imaging media into the nucleus 24 from more than one approach in some instances.

Referring now to FIG. 4, the injector 200 is shown with the plunger 208 partially depressed and the imaging media 204 being introduced into the nucleus. In the present embodiment, the imaging media 204 is a saline and/or radiographic contrast medium such as sodium diatrizoate solution sold under the trademark Hypaque® by Amersham Health, a division of GE Healthcare (Amersham, UK), (NEEDLE Patterns; Mechanical Dislodging). Other suitable imaging media 204 are utilized in other instances. While the imaging media 204 is shown as being injected by injector 200, generally the imaging media 204 may be injected in any suitable way, including under pressure supplied by a hand, electric, or other type of powered pressurization device in some instances. In some instances, an intradiscal pressure is monitored as the imaging media 204 is introduced into the nucleus 24. Accordingly, in some instances the imaging media 204 is introduced into the nucleus 24 until the intradiscal pressure reaches a predetermined pressure or range of pressures. In some instances, the predetermined intradiscal pressure is between about 0.1 MPa (14.5 psi) and about 4.6 MPa (667.2 psi). In some instances, the predetermined intradiscal pressure is between about 0.3 MPa (43.5 psi) and about 2.3 MPa (333.6 psi). As the imaging media 204 is introduced into the nucleus 24, the increased intradiscal pressure causes the endplates 16, 18 of the adjacent vertebra 12, 14 to distract in some instances. A pressure gauge and/or a pressure limiter is used in some instances to avoid over inflation or excessive injection. Further, in some instances the patient's pain is monitored during introduction of the imaging media.

Referring again to FIG. 2, after introducing the imaging media 204 into the nucleus 24 at step 102, the method 100 continues at step 104 where images of the intervertebral disc 20 are obtained. In that regard, the imaging media 204 is utilized to obtain images of the nucleus 24 in some instances. The images of the nucleus 24 are utilized to identify fissures, cracks, tears, leaks, and/or other malformations in the nucleus 24 and/or the annulus 22. In some instances, CT, X-ray, and/or MRI scans are utilized to obtain the images of the intervertebral disc 20. In other instances, other suitable medical imaging techniques are utilized.

After obtaining images of the intervertebral disc at step 104, the method 100 continues at step 106 where the imaging media is aspirated or removed from the nucleus. Referring to FIG. 5, in some instances the imaging media 204 is aspirated from the nucleus 24 using an evacuation system 214. In the illustrated embodiment, the evacuation system 214 is shown attached to the needle 212. In that regard, the same needle 212 used to inject the imaging media 204 is utilized to remove the imaging media in some instances. Further, in some instances the needle 212 remains within the patient during the imaging procedure at step 104. In that regard, in some instances the needle 212 is retracted from at least the nucleus 24, but remains at least partially positioned within the patient during imaging. In other instances, the needle 212 remains within the nucleus 24 during imaging. In some instances, the needle 212 is radiopaque. In other instances, the needle 212 is radiolucent.

Where the needle 212 is utilized by the evacuation system 214, the injector body 202 is disengaged from the needle 212 and tubing 216 of the evacuation system is engaged or connected to the needle. In the illustrated embodiment, a distal portion 218 of the tubing 216 is threadingly engaged with the needle 212. Generally, however, any suitable connection between the tubing 216 and the needle 212 is utilized, including luer connections, valve connections, snap-fit connections, crimp connectors, zip ties, and/or other connections. In that regard, in many instances the connection between the tubing 216 and the needle 212 is substantially similar to the connection between the main body 202 of the injector 200 and the needle 212. In some instances, the tubing 216 attaches or engages with the main body 202 of the injector 200. For example, in some instances the tubing 216 engages with the proximal portion 206 of the main body 202. In such instances, the needle 212 and the main body 202 may be integrally formed.

In the illustrated embodiment of FIG. 5, the tubing 216 of the evacuation system 214 extends from the needle 212 to a reservoir 220 for receiving the evacuated materials from the nucleus. Generally, the reservoir 220 is a suitable for receiving and holding the evacuated imaging media and other flowable materials from the nucleus 24. In some instances, the reservoir 220 is a can, tube, bag, pouch, or other suitable container formed of a medical grade material, such as a suitable polymer or metal. In some instances, the reservoir 220 is transparent and/or translucent to allow visualization of the amount of material contained within the reservoir. In that regard, in some instances the reservoir 220 is relative rigid and graduated such that the amount of evacuated materials can be measured. In other instances, the reservoir 220 is semi-flexible or flexible.

In the illustrated embodiment, the reservoir 220 is shown as receiving the imaging media 204. It is understood, however, that other flowable materials from the nucleus 24 are evacuated along with the imaging media 204. In that regard, in some instances the size of the needle 212 is selected to prevent removal of solid tissue from the nucleus 24. For example, in some instances the needle 212 is an 14 gauge needle or smaller. In some instances the needle 212 is an 18 gauge needle or smaller. In some instances, the needle 212 is a 20 gauge needle or a 22 gauge needle. Accordingly, in some instances the needle 212 has a maximum outer diameter less than about 1.7 mm, less than about 1.3 mm, or less than about 0.9 mm. Similarly, in some instances the needle 212 has a maximum inner diameter or lumen diameter less than about 1.3 mm, less than about 0.9 mm, or less than about 0.6 mm. The maximum inner diameter of the needle 212 is selected in some instances based on the maximum size of material that is to be removed from the nucleus 24 during evacuation. Accordingly, in some instances, the maximum inner diameter of the needle 212 is selected to allow only materials having a diameter of about 0.5 mm or less to be evacuated through the needle. In other instances, only materials having a diameter less than about. 0.3 mm or less are to be evacuated. In other instances, materials having a diameter less than about 1.0 mm are to be evacuated.

Further, generally the outer diameter of the needle 212 is selected such that the needle can be introduced through the annulus 22 and removed from the annulus without requiring a repair of the annulus with a plug, suture, or otherwise. That is, the outer diameter of the needle 212 is sufficiently small to allow the annulus 22 to self-seal upon removal of the needle. In some instances, however, it may be necessary to repair an opening in the annulus 22 left by use of the needle 212. In such instances, an annulus plug or annulus repair as described in U.S. patent application Ser. No. 11/412,272 titled "Devices, Apparatus, and Methods for Bilateral Approach to Disc Augmentation" and filed Apr. 27, 2006; U.S. patent application Ser. No. 11/412,558 titled "Devices, Apparatus, and Methods for Improved Disc Augmentation" and filed Apr. 27, 2006; and U.S. patent Application Ser. No. 11/621, 173 titled "Devices, Apparatus, and Methods for Disc Augmentation" and filed Jan. 9, 2007, each of which is hereby incorporated by reference in its entirety, may be utilized.

The reservoir 220 is in communication with a vacuum source 222. In the illustrated embodiment, the vacuum source 222 is connected to the reservoir 220 via tubing 224. In some instances, tubing 224 is substantially similar to tubing 216. In that regard, in some embodiments the tubing 216, 224 is flexible medical grade tubing. In other instances, the tubing 216, 224 is rigid or semi-flexible. Generally, the tubing 216, 224 is made of a suitable medical grade metal or polymer and includes appropriate connectors at its ends to maintain a secure connection with the needle 212, reservoir 220, and/or vacuum source 222. In that regard, the tubing 216, 224 may be connected to the needle 212, reservoir 220, and/or vacuum source 222 with one or more of the following types of connections: threaded connections, luer connections, valve connections, snap-fit connections, crimp connectors, zip ties, and/or other connections. In other instances, the vacuum source 222 and the reservoir 220 are integrated into a single unit or device. Generally, the vacuum source 222 is any suitable vacuum source for removing the imaging media 204 and/or other flowable materials from the nucleus 24.

In some instances, the evacuation system 214 is a disposable system. Accordingly, in some instances all of the components of the evacuation system 214 are disposable. In such instances, the vacuum source 222 may comprise a syringe, a hand pump, a powered vacuum pump, and/or other disposable vacuum source. In that regard, it is desirable in some instances for the vacuum source 222 to be small and cost-effective as a one-time use device. In some instances, the tubing 216, 224 and the reservoir 220 are disposable, while the vacuum source 222 is a reusable device. In that regard, in some instances the vacuum source 222 is a vacuum line installed in an operating room or other medical facility. In other instances, the vacuum source is a syringe, a hand pump, a powered vacuum pump, and/or other reusable vacuum source. Further, it is understood that the components of the evacuation system 214 may be of any suitable length and/or size and be spaced with respect to one another in any suitable manner. Accordingly, it is understood that FIG. 5 is not necessarily drawn to scale.

Referring now to FIG. 6, the evacuation system 214 is utilized to remove substantially all of the imaging media 204 and/or other flowable media from the nucleus. The needle 212 is moved around within the nucleus 24 in some embodiments to ensure that the imaging media 204 and/or other flowable media are removed from substantially all portions of the nucleus. Further, as discussed above, in some instances it is desirable to limit the size of the material removed from the nucleus in order to preserve as much solid natural nucleus tissue as possible. Accordingly, in some instances the opening of the needle 212 becomes blocked by larger materials. Thus, in some instances the vacuum source is actuated intermittently in order to release any larger materials that may block the end of the needle 212. In some instances, a back pressure (i.e., pressure in the opposite direction of the vacuum source) is applied through the needle to urge any such materials away from the end of the needle 212 to allow flow of the flowable materials through the needle to the reservoir 220.

Referring again to FIG. 2, after aspirating the imaging media and/or other flowable materials from the nucleus at step 106, the method 100 continues at step 108 where a disc augmentation biomaterial is introduced into the nucleus. Generally, any suitable disc augmentation biomaterial may be utilized. For example, in some instances the disc augmentation biomaterial includes one or more of protein-based biomaterials, collagen-based biomaterials, fibrin-based biomaterials, albumin-based biomaterials, elastin-based biomaterials, silk-based biomaterials, polysacharide-based biomaterials; hydrogel-based biomaterials, hydrophillic polymers, elastomeric polymers, silicone, polyurethane, silicone-polyurethane copolymers, and polyolefin-based biomaterials. In some instances collagen-based biomaterials are utilized. For example, in some instances collagen-based biomaterials and the associated methods disclosed in U.S. patent application Ser. No. 10/245,955 titled "Collagen-Based Materials and Methods for Augmenting Intervertebral Discs" and filed Sep. 18, 2002; U.S. patent application Ser. No. 11/030,705 titled "Compositions and Methods for Treating Intervertebral Discs with Collagen-Based Materials" and filed Jan. 6, 2005; U.S. patent application Ser. No. 11/117,025 titled "Collagen-Based Materials and Methods for Augmenting Intervertebral Discs" and filed Apr. 28, 2005; U.S. patent application Ser. No. 11/479,916 titled "Collagen Delivery Device" and filed Jun. 30, 2006; and U.S. patent application Ser. No. 11/480,116 titled "Method of Treating a Patient Using a Collagen Material" and filed Jun. 30, 2006, each of which is incorporated by reference in its entirety, are utilized.

Examples of biocompatible materials that are used for disc augmentation in some instances include natural or synthetic and resorbable or non-resorbable materials. Natural materials include various forms of collagen that are derived from collagen-rich or connective tissues such as an intervertebral disc, fascia, ligament, tendon, skin, or demineralized bone matrix. Material sources include autograft, allograft, xenograft, or human-recombinant origin materials. Natural materials also include various forms of polysaccharides that are derived from animals or vegetation such as hyaluronic acid, chitosan, cellulose, or agar. Other natural materials include other proteins such as fibrin, albumin, silk, elastin and keratin. Synthetic materials include various implantable polymers or hydrogels such as silicone, polyurethane, silicone-polyurethane copolymers, polyolefin, polyester, polyacrylamide, polyacrylic acid, polyvinyl alcohol, polyethylene oxide, polyethylene glycol, polylactide, polyglycolide, poly(lactide-co-glycolide), poly(dioxanone), poly(.epsilon.-caprolactone), poly(hydroxylbutyrate), poly(hydroxylvalerate), tyrosine-based polycarbonate, polypropylene fumarate or combinations thereof. Suitable hydrogels may include poly (vinyl alcohol), poly(acrylic acids), poly(methacrylic acids), copolymers of acrylic acid and methacrylic acid, poly(acrylonitrile-acrylic acid), polyacrylamides, poly(N-vinyl-2-pyrrolidone), polyethylene glycol, polyethyleneoxide, polyacrylates, poly(2-hydroxy ethyl methacrylate), copolymers of acrylates with N-vinyl pyrrolidone, N-vinyl lactams, polyurethanes, polyphosphazenes, poly(oxyethylene)-poly(oxypropylene) block polymers, poly(oxyethylene)-poly(oxypropylene) block polymers of ethylene diamine, poly(vinyl acetate), and sulfonated polymers, polysaccharides, proteins, and combinations thereof.

The selected biocompatible material may be curable or polymerizable in situ. The biocompatible material may transition from a flowable to a non-flowable state shortly after injection. One way to achieve this transition is by adding a crosslinking agent to the biomaterial before, during, or after injection. The biocompatible material in its final state may be load-bearing, partially load-bearing, or simply tissue augmenting with minimal or no load-bearing properties.

Proteoglycans may also be included in the injectable biocompatible material 48 to attract and/or bind water to keep the nucleus 24 hydrated. Regenerating agents may also be incorporated into the biocompatible material. An exemplary regenerating agent includes a growth factor. The growth factor can be generally suited to promote the formation of tissues, especially of the type(s) naturally occurring as components of an intervertebral disc. For example, the growth factor can promote the growth or viability of tissue or cell types occurring in the nucleus pulposus, such as nucleus pulposus cells and chondrocytes, as well as space filling cells, such as fibroblasts and connective tissue cells, such as ligament and tendon cells. Alternatively or in addition, the growth factor can promote the growth or viability of tissue types occurring in the annulus fibrosis, as well as space filling cells, such as fibroblasts and connective tissue cells, such as ligament and tendon cells. An exemplary growth factor can include transforming growth factor-$\beta$ (TGF-$\beta$) or a member of the TGF-$\beta$ superfamily, fibroblast growth factor (FGF) or a member of the FGF family, platelet derived growth factor (PDGF) or a member of the PDGF family, a member of the hedgehog family of proteins, interleukin, insulin-like growth factor (IGF) or a member of the IGF family, colony stimulating factor (CSF) or a member of the CSF family, growth differentiation factor (GDF), cartilage derived growth factor (CDGF), cartilage derived morphogenic proteins (CDMP), bone morphogenetic protein (BMP), or any combination thereof. In particular, an exemplary growth factor includes transforming growth factor P protein, bone morphogenetic protein, fibroblast growth factor, platelet-derived growth factor, insulin-like growth factor, or any combination thereof.

Further, therapeutic and/or biological agents may also be incorporated into the biomaterial. An exemplary therapeutic or biological agent can include a soluble tumor necrosis factor $\alpha$-receptor, a pegylated soluble tumor necrosis factor $\alpha$-receptor, a monoclonal antibody, a polyclonal antibody, an antibody fragment, a COX-2 inhibitor, a metalloprotease inhibitor, a glutamate antagonist, a glial cell derived neurotrophic factor, a B2 receptor antagonist, a substance P receptor (NK1) antagonist, a downstream regulatory element antagonistic modulator (DREAM), iNOS, a inhibitor of tetrodotoxin (TTX)-resistant Na+-channel receptor subtypes PN3 and SNS2, an inhibitor of interleukin, a TNF binding protein, a dominant-negative TNF variant, Nanobodies™, a kinase inhibitor, or any combination thereof. These regenerating, therapeutic, or biological agents may promote healing, repair, regeneration and/or restoration of the disc, and/or facilitate proper disc function. Additives appropriate for use in the claimed invention are known to persons skilled in the art, and may be selected without undue experimentation.

Referring to FIG. 7, in some instances an injector 230 is utilized at step 108. In the illustrated embodiment, the injector 230 comprises a main body 232 that houses a disc augmentation biomaterial 234. A proximal portion 236 of the main body 232 receives a plunger 238 that is moveable along the longitudinal axis of the main body to urge the biomaterial 234 out of a distal portion 240 of the main body. In the illustrated embodiment, the distal portion 240 of the main body 232 is engaged with a hypodermic needle 242. In particular, the distal portion 240 of the main body 232 is threadingly engaged with a hypodermic needle 242. Accordingly, the biomaterial 234 that is urged out of the distal portion 240 of the main body 232 passes into the needle 242 upon distal advancement of the plunger 238 into the main body.

Generally the needle 242 is selected such that the needle can be introduced through the annulus 22 and removed from the annulus without creating an opening that requires repair of the annulus. That is, the outer diameter of the needle 242 is sufficiently small to allow the annulus 22 to self-seal upon removal of the needle. In some instances the size of the needle 242 is selected to based on the size of the particles comprising the disc augmentation biomaterial 234. For example, in some instances where the biomaterial 234 has particles up to 1.5 mm in diameter the needle 242 is a 8, 10, 12, or 14 gauge needle. In other instances, where the biomaterial has particles up to 0.5 mm in diameter the needle 242 is a 18 or 20 gauge needle. Generally, the smallest suitable needle size is utilized to inject the biomaterial. Accordingly, in some instances the needle 242 has a maximum outer diameter less than about 3.3 mm, less than about 2.6 mm, 2.0 mm, or less than about 1.3 mm. Similarly, in some instances the needle 242 has a maximum inner diameter or lumen diameter less than about 2.9 mm, 2.2 mm, 1.6 mm, or less than about 0.9 mm. In some instances, the needle 242 is the same needle 212 utilized in injecting the imaging media and/or removing the imaging media and/or flowing material from the nucleus. In one particular embodiment, a single needle is utilized for all three of injecting the imaging media, aspirating the imaging media, and injecting the disc augmentation biomaterial. In such instances, the injector 200, the evacuation system 214, and the injector 230 are each selectively coupled to the needle as necessary during the various method steps.

Referring to FIG. 8, the injector 230 is utilized to introduce the disc augmentation biomaterial 234 into the nucleus 24 of the intervertebral disc 20 in some instances. In that regard, the hypodermic needle 242 is advanced through the annulus 22 and into the nucleus 24 as shown. Once the distal end of the needle 242 is positioned within the nucleus 24, the plunger 208 is depressed to inject the biomaterial 234 into the nucleus. In some instances, the distal end of the needle 242 is moved around within the nucleus 24 during injection of the biomaterial 234 to encourage distribution of the biomaterial throughout the nucleus. In some instances the imaging media is introduced without removing any of solid tissue of the nucleus 24 beforehand. That is, a partial or total nucleotomy is not performed prior to injection of the biomaterial 234 in some instances. However, as described above, flowable nucleus material is evacuated along with the imaging media in some instances. This approach allows preservation of a maximum amount of the patient's natural solid nucleus tissue.

In some instances, the biomaterial 234 is introduced into an inflatable device positioned within the nucleus 24. In this manner the inflatable device is utilized to contain the biomaterial 234. In some instances, the inflatable device is permeable such that the biomaterial 234 is able to flow out of the inflatable device over time. In some instances, the inflatable device is bioresorbable such that the inflatable device is absorbed or otherwise removed from the nucleus while the biomaterial stays within the nucleus after the inflatable device is absorbed or otherwise removed over time. In some instances, the introduction of the disc augmentation biomaterial is as described in one or more of the following: U.S. patent application Ser. No. 10/314,396 titled "Method and Apparatus for Intervertebral Disc Expansion" and filed Dec. 7, 2002; U.S. patent application Ser. No. 11/412,272 titled "Devices, Apparatus, and Methods for Bilateral Approach to Disc Augmentation" and filed Apr. 27, 2006; U.S. patent application Ser. No. 11/412,558 titled "Devices, Apparatus, and Methods for Improved Disc Augmentation" and filed Apr. 27, 2006; U.S. patent application Ser. No. 11/621,173 titled "Devices, Apparatus, and Methods for Disc Augmentation" and filed Jan. 9, 2007; and U.S. patent application Ser. No. 11/924,026 titled "Method and Apparatus for Intervertebral Disc Expansion" and filed Oct. 25, 2007, each of which is hereby incorporated by reference in its entirety.

The introduction of the biomaterial 234 continues until the treating medical personnel is satisfied with the disc augmentation. This determination is made subjectively in some instances. In other instances, objective measures such as disc height, intradiscal pressure, volume of biomaterial injected, and/or other objective measurements are utilized to determine when introduction of the biomaterial 234 is complete. In some instances, the In some instances, the introduction of the biomaterial is facilitated by using a pressurization device and monitoring gauge. In that regard, in some instances an intradiscal pressure is monitored as the biomaterial 234 is introduced into the nucleus 24. Accordingly, in some instances the biomaterial 234 is introduced into the nucleus 24 until the intradiscal pressure reaches a predetermined pressure or range of pressures. In some instances, the predetermined intradiscal pressure is between about 0.1 MPa (14.5 psi) and about 2.3 MPa (333.6 psi). In some instances, the predetermined intradiscal pressure is between about 0.3 MPa (43.5 psi) and about 1.3 MPa (188.6 psi). As the biomaterial 234 is introduced into the nucleus 24, the increased intradiscal pressure causes the endplates 16, 18 of the adjacent vertebra 12, 14 to distract in some instances. A pressure gauge and/or a pressure limiter is used in some instances to avoid over inflation or excessive injection.

In some instances, the biomaterial 234 is introduced after the imaging media 204 has been aspirated or removed from the nucleus 24. In other instances, the biomaterial 234 is introduced while the imaging media 204 is being removed from the nucleus 24. In some instances, the biomaterial 234 is injected through the injector 230 and needle 242 while the evacuation system 214 and needle 212 are utilized to remove the imaging media 234 and other flowable material from the nucleus 24. In that regard, in some instances the needles 212, 242 are inserted into the disc space from different surgical approaches. In one particular embodiment, the needle 212 is inserted from a first oblique posterior-lateral approach while the needle 242 is inserted from a second oblique posterior-lateral approach. In one such instances, the needles 212, 242 are inserted bilaterally.

After the biomaterial 234 is injected into the nucleus, the needle 242 is removed. In some instances where the selected biomaterial 234 is curable in situ, the needle 242 is removed during or after curing to minimize leakage. As discussed above, any openings created by introduction of the needles 212, 242 are small enough that they will close or self-seal sufficiently that the injected biomaterial 234 will remain within the nucleus 24 bound by the annulus 22. In some instances, an annulus closure device such as a suture, a plug, or a material sealant is utilized. Further, as discussed above, in some instances the nucleus 24 is accessed by inserting a cannula or guide sheath (not shown) into the patient and locating the cannula at or near the annulus 22. In some instances, the needle 242 is advanced through the cannula or guide sheath before piercing the annulus 22 to reach the nucleus 24. In other instances, an accessing instrument, such as a trocar needle or a K-wire is inserted through the cannula and used to penetrate the annulus, creating an opening in the annulus 22 through which the needle 242 and/or needle 212 will be introduced into the nucleus 24. It is understood that any cannulated instrument including a guide needle or a trocar sleeve may be used to guide the accessing instrument. In such instances, the cannula or guide sheath is removed and the minimally invasive surgical incision is closed.

In some instances, the steps of the method 100, especially introduction of the imaging media, aspiration of the imaging media, and introduction of the disc augmentation biomaterial, are monitored and guided with the aid of imaging methods such as fluoroscopy, x-ray, computed tomography, magnetic resonance imaging, and/or image guided surgical technology such as a Stealth Station surgical navigation system (Medtronic, Inc., Minneapolis, Minn.) or a BrainLab system (Heimstetten, Germany). In one particular embodiment, the introduction of the imaging media is monitored to detect leaks, fissures, and/or other characteristics that are identifiable from the flow of the imaging media into the nucleus.

Referring generally now to FIGS. 9-12, shown therein are various ends or tips for the needles, cannulas, or other lumen devices utilized to introduce materials into and/or remove materials from the nucleus. It is understood that each of the tips may be applied to both beveled and non-beveled devices. Further, with respect to beveled devices, the bevels may be standard, elongated, short, true short, or otherwise.

Referring more particularly to FIG. 9, shown therein is an end portion 300 according to one aspect of the present disclosure. As illustrated, the end portion 300 includes an outer surface 302 and an opposing inner surface 304. As discussed above, the size of the needle, cannula, or other device is dependent on the associated materials in some instances. For example, in some embodiments, the size is selected to prevent removal of solid tissue from the nucleus. In other embodiments, the size is selected to allow introduction of a biomaterial having particles of a certain size. Accordingly, the outer diameter 306 and the inner diameter 308 of the end portion 300 are selected accordingly. In some instances, the outer diameter 306 is between about 0.4 mm and about 3.3 mm. In some instances, the outer diameter 306 is between about 0.7 mm and about 1.3 mm. Similarly, in some instances the inner diameter is between about 0.2 mm and about 2.9 mm. In some instances, the inner diameter is between about 0.3 mm and about 0.8 mm. While the end portion 300 is shown as having a substantially circular or cylindrical profile, in other embodiments the end portion 300 has other profiles including, arcuate, triangular, rectangular, or otherwise.

Referring more particularly to FIG. 10, shown therein is an end portion 310 according to one aspect of the present disclosure. In some aspects the end portion 310 is substantially similar to the end portion 300 of FIG. 9. However, the end portion 310 includes a filter or screen 312. The filter 312 is utilized limit the size of the tissues removed from the nucleus in some instances. In other instances, the filter 312 is utilized to limit the size of the materials introduced into the nucleus. In that regard, the size of the openings of the filter 312 are selected based on the corresponding size of the material and/or particles that the filter is intended to stop. In the present embodiment, the openings of the of the filter of substantially constant size. In other instances, the size of the openings vary across the filter. Generally, the opening sizes vary between about 0.1 mm to about 1.0 mm.

Referring more particularly to FIG. 11, shown therein is an end portion 320 according to another aspect of the present disclosure. In some aspects the end portion 320 is similar to the end portions 300 and 310 described above. However, the end portion 320 includes a plurality of lumens 322, 324, 326, 328, 330, and 332. In that regard, the lumen 322 encompasses the other lumens 324, 326, 328, 330, and 332. In the illustrated embodiment, at least lumens 324, 326, 328, and 332 are of a substantially similar size. Lumen 330 is of a slightly smaller size. Generally, the plurality of lumens are of substantially the same size or of varying sizes. With respect to material extraction from the nucleus, having a plurality of lumens increases the flow of material from the nucleus while limiting the size of the material evacuated in some instances. In that regard, the size of the lumens limits the size of the material that can be evacuated from the nucleus while the plurality of lumens allows removal of material even when one of the lumens becomes clogged or otherwise prevented from removing material from the nucleus. Further, vacuum suction is applied to the lumens 322, 324, 326, 328, 330, and 332 individually in some instances. In other instances, the lumens 322, 324, 326, 328, 330, and 332 collectively receive vacuum suction.

While the illustrated embodiment of FIG. 11 includes one outer lumen containing five inner lumens, generally any number of lumens may be utilized. In some instances, the end portion 320 is a dual lumen device. The dual lumen device is concentric (one lumen around the other lumen) in some instances. In other instances, the dual lumen device is bilateral (one lumen next to the other lumen). In some instances, a dual-lumen or other multi-lumen needle is utilized to evacuate flowable media from the nucleus and inject the biomaterial into the nucleus. In some such instances, one or more of the lumens is utilized exclusively for evacuating material while one or more of the other lumens is utilized exclusively for introducing the biomaterial.

Referring more particularly to FIG. 12, shown therein is an end portion 340 according to another aspect of the present disclosure. In some aspects the end portion 340 is similar to the end portions 300, 310, and 320 described above. In particular, lumen 342 is substantially similar to end portion 300 and/or lumen 322 in some instances. However, the end portion 340 also includes an outer sheath 344 surrounding lumen 342. In some instances, the sheath 344 is a guide sheath positioned adjacent the annulus and outside of the nucleus. In other instances, the sheath is positioned within the nucleus. The lumen 342 is movable with respect to the sheath 344. In particular, the lumen 342 is movable along the longitudinal axis with respect to the sheath 344 such that the amount of the lumen extending beyond the end of the sheath, if any, is selectively determined by a user. In the illustrated embodiment, the inner diameter of sheath 344 substantially matches the outer diameter of lumen 342. In that regard, in some instances the lumen 342 is retracted within the sheath 344 to dislodge material blocking the end of the lumen during extraction of flowable material from the nucleus. Accordingly, in some instances upon noticing a stoppage or slowing of the flow of material from the nucleus a user retracts the lumen 342 into the sheath 344 to dislodge any pieces of material that are blocking the opening of the lumen 342.

In some instances, the end portion 340 includes a mechanical device that is actuated to dislodge the pieces of material blocking the opening of the lumen 342. In that regard, in some instances the mechanical device is a single blade, bar, rod, or otherwise that is actuatable by a user to move across the opening of the lumen 342. In some instances the mechanical devices functions in a manner similar to a windshield wiper on a vehicle. In some instances, the mechanical device is part of or carried by the outer sheath 344.

The end portions 300, 310, 320, and 340 described with respect to FIGS. 9, 10, 11, and 12 are exemplary and should not be considered limiting. Other suitable end portions for the needles, cannulas, and/or other lumen devices of the present disclosure are. Further, it is understood that one or more of the various features of the end portions 300, 310, 320, and/or 340 are combined in a single end portion in some instances. Further, it is understood that the end portions 300, 310, 320, and/or 340 include one or more openings positioned around and/or along the needle in some instances to facilitate introduction or extraction of materials into or from the intervertebral disc.

Figure 13:
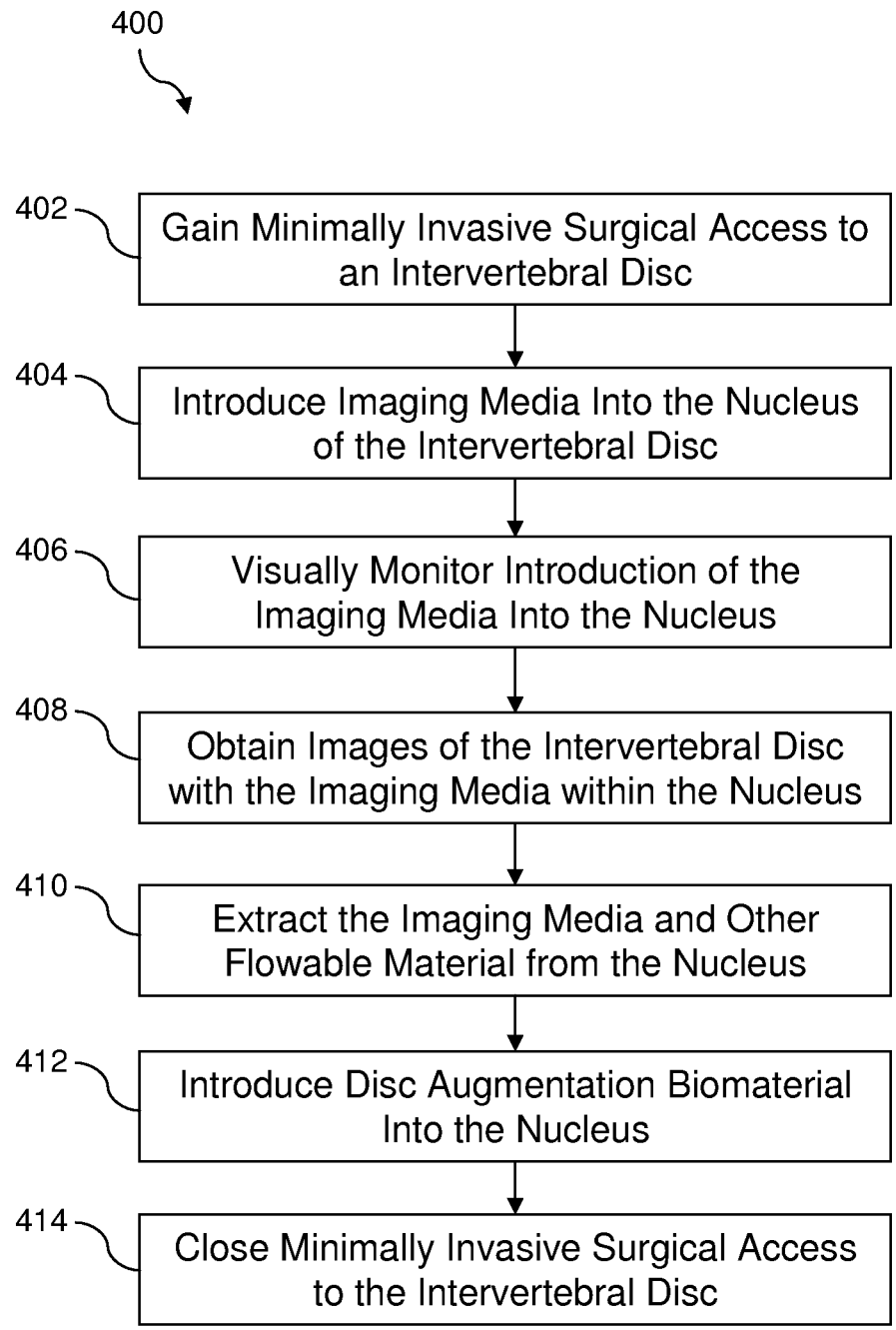
FIG. 13 is a flowchart illustrating a method of treating an intervertebral disc according to another aspect of the present disclosure.

Referring now to FIG. 13, a method 400 for treating an intervertebral disc according to one aspect of the present disclosure is disclosed. In particular, FIG. 13 is a flowchart illustrating generally the steps of the method 400. In some aspects the steps of the method 400 are similar to aspects of the method 100 and corresponding apparatus described above. Accordingly, additional detail regarding the steps of the method 400 are available from the disclosure above.

The method 400 begins at step 402 where access to an intervertebral disc is gained through a minimally invasive surgical access. At step 404, an imaging media is introduced through the minimually invasive surgical access and into the nucleus of the intervertebral disc. The introduction of the imaging media into the nucleus is monitored visually at step 406. In that regard, in some instances steps 404 and 406 are performed substantially simultaneously. The method 400 continues with step 408 where images of the intervertebral disc are obtained with the imaging media located within the nucleus. After the imaging, the method 400 continues at step 410 where the imaging media and other flowable material are extracted from the nucleus. In some instances, the imaging media and flowable material are extracted using an vacuum extractor. The method 400 continues at step 412 with the introduction of disc augmentation biomaterial into the nucleus. In some instances the disc augmentation biomaterial is introduced simultaneously with the extraction of imaging media. After the biomaterial has been introduced to sufficiently augment the intervertebral disc, the method 400 continues with step 414 where the minimally invasive surgical access to the intervertebral disc is closed.

Figure 14:
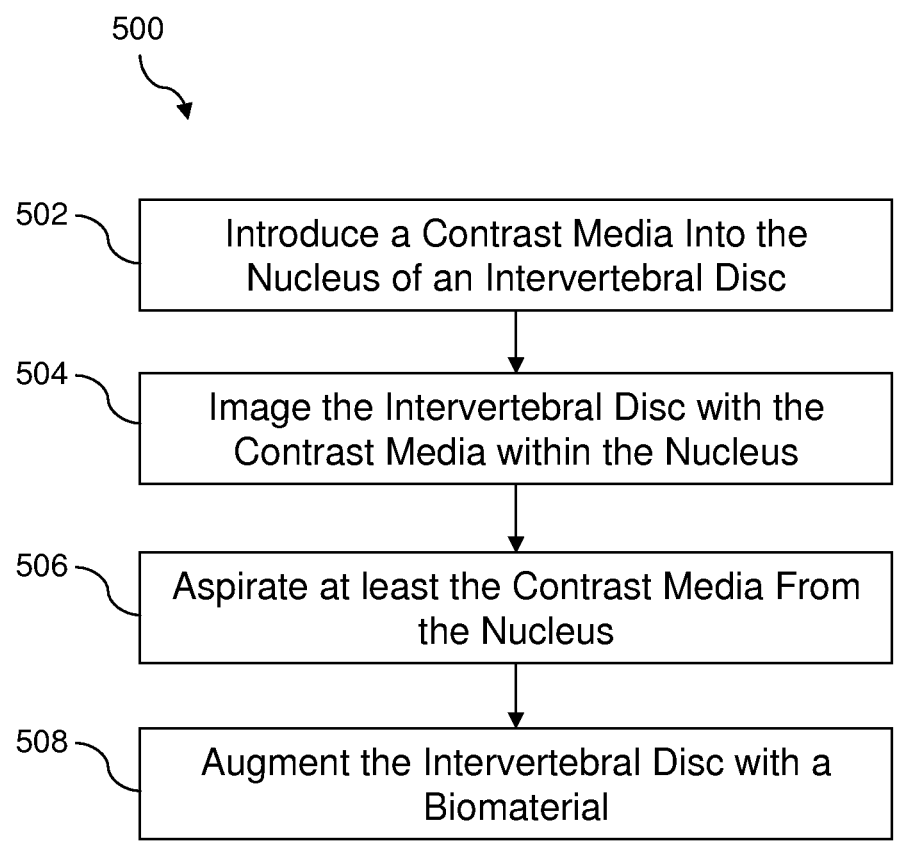
FIG. 14 is a flowchart illustrating a method of treating an intervertebral disc according to another aspect of the present disclosure.

Referring now to FIG. 14, a method 500 for treating an intervertebral disc according to one aspect of the present disclosure is disclosed. In particular, FIG. 14 is a flowchart illustrating generally the steps of the method 500. In some aspects the steps of the method 500 are similar to aspects of the methods 100 and 400 and the corresponding apparatus described above. Accordingly, additional detail regarding the steps of the method 500 are available from the disclosure above.

The method 500 begins at step 502 where a contrast media is introduced into the nucleus of an intervertebral disc. The method 500 continues with step 504 where images of the intervertebral disc are obtained with the contrast media located within the nucleus. After the imaging, the method 500 continues at step 506 where at least the contrast media is extracted from the nucleus. In some instances, the contrast media is extracted using an vacuum extractor. The method 500 continues at step 508 where the intervertebral disc is augmented with a biomaterial. In some instances, the biomaterial is injected into the nucleus of the intervertebral disc. In some instances the biomaterial is introduced simultaneously with the extraction of contrast media.

It is understood that the steps of the methods 100, 400, and 500 of the present disclosure are performed in a single surgical procedure in some instances. In other instances, the steps of the methods 100, 400, and 500 are performed on the same day or within a few hours of one another in multiple surgical procedures. Accordingly, the methods 100, 400, and 500 of the present disclosure for treating an intervertebral disc provide added convenience to both the patient and treating medical personnel compared to currently available treatments.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. Further, it is understood that various aspects of the different embodiments are combined in some instances into a single embodiment. For example, in some instances one or more steps of one embodiment are combined with one or more steps of one or more other embodiments. Similarly, in some instances one or more components of one embodiment are combined with one or more components of one or more other embodiments. It is understood that all spatial references, such as "horizontal," "vertical," "top, upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method of treating an intervertebral disc of a patient, comprising:

introducing a contrast media through an annulus and directly into a nucleus of the intervertebral disc via a first hypodermic needle having a maximum outer diameter less than about 1.7 mm such that the contrast media disperses within an interior of the nucleus, the contrast media being introduced without any of the annulus or nucleus being removed beforehand;

imaging the intervertebral disc with the contrast media within the nucleus;

evacuating the contrast media and other flowable material from the nucleus via vacuum extraction applied using a vacuum source positioned outside the patient, the vacuum extraction being applied to the nucleus through a second hypodermic needle having a maximum outer diameter less than about 3.3 mm, the second hypodermic needle having a distal portion for positioning within the nucleus and an opposing proximal portion for positioning outside the intervertebral disc, the proximal portion of the second needle in communication with a reservoir for receiving the evacuated contrast media and flowable material; and introducing a disc augmentation biomaterial into the nucleus through the annulus and into the nucleus of the intervertebral disc via a third hypodermic needle having a maximum outer diameter less than about 3.3 mm such that the disc augmentation biomaterial is maintained within the nucleus without having to repair an opening in the annulus;

wherein the first and second hypodermic needles are retracted from the intervertebral disc before imaging.

2. The method of claim 1, wherein the first needle is used for both introducing the contrast media and evacuating the contrast media.

3. The method of claim 2, wherein at least a portion of the needle used for both introducing the contrast media and evacuating the contrast media is positioned within the patient during the imaging step.

4. The method of claim 3, wherein at least a portion of the needle used for both introducing the contrast media and evacuating the contrast media is reintroduced into the nucleus after the imaging step.

5. The method of claim 4, wherein evacuating the contrast media and other flowable material from the nucleus comprises moving the needle around within the nucleus.

6. The method of claim 5, wherein the vacuum extraction is applied intermittently to prevent clogging of the needle.

7. The method of claim 1, wherein the vacuum source is in communication with the reservoir.

8. The method of claim 1, wherein introducing a disc augmentation biomaterial into the nucleus comprises injecting a material selected from the group consisting of protein-based biomaterials, collagen-based biomaterials, fibrin-based biomaterials, albumin-based biomaterials, elastin-based biomaterials, silk-based biomaterials, polysacharide-based biomaterials; hydrogel-based biomaterials, hydrophillic polymers, elastomeric polymers, silicone, polyurethane, silicone-polyurethane copolymers, and polyolefin-based biomaterials.

9. The method of claim 1, wherein introducing a disc augmentation biomaterial into the nucleus comprises injecting the disc augmentation material into an inflatable balloon positioned within the nucleus.

10. A method of treating an intervertebral disc of a patient, comprising:

introducing a contrast media directly into a nucleus of the intervertebral disc via a hypodermic needle such that the contrast media disperses within an interior of the nucleus, the contrast media being introduced without removing any of the nucleus;

imaging the intervertebral disc with the contrast media within the nucleus;

aspirating at least the contrast media from the nucleus via vacuum suction applied using a vacuum source positioned outside the patient to reduce an intradiscal pressure within the nucleus; and introducing a disc augmentation biomaterial into the nucleus, the disc augmentation biomaterial introduced in a manner such that the disc augmentation biomaterial is maintained within the nucleus without having to repair an opening in an annulus surrounding the nucleus;

wherein the hypodermic needle is retracted from the intervertebral disc prior to imaging.

11. The method of claim 10, wherein introducing the disc augmentation material comprises introducing disc augmentation material until the intradiscal pressure reaches a predetermined range.

12. The method of claim 11, wherein the contrast media is aspirated through a cannula via vacuum suction to a reservoir.

13. The method of claim 12, wherein the cannula comprises a filter at a distal end to limit the aspiration to flowable materials and prevent aspiration of solid tissue larger than a predetermined size.

14. The method of claim 12, wherein a filter prevents aspiration of solid tissue with a diameter larger than about 0.5 mm.

15. The method of claim 14, wherein aspirating the flowable materials from the nucleus comprises moving the cannula around within the nucleus.

16. The method of claim 15, wherein the vacuum suction is applied intermittently to prevent clogging of the filter.

17. The method of claim 12, wherein the cannula comprises a plurality of openings to enhance aspiration and prevent clogging of the cannula.

18. The method of claim 1, wherein the vacuum source is a vacuum line installed in an operating room or other medical facility.

* * * * *